(12) United States Patent
Perez et al.

(10) Patent No.: US 7,274,458 B2
(45) Date of Patent: Sep. 25, 2007

(54) THERMOPLASTIC FILM HAVING METALLIC NANOPARTICLE COATING

(75) Inventors: Mario A. Perez, Burnsville, MN (US); Donald J. McClure, Shoreview, MN (US); Rajdeep S. Kalgutkar, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 257 days.

(21) Appl. No.: 11/073,787

(22) Filed: Mar. 7, 2005

(65) Prior Publication Data

US 2006/0197953 A1    Sep. 7, 2006

(51) Int. Cl.
*G01N 21/55* (2006.01)
*G01J 1/04* (2006.01)
*G01J 5/08* (2006.01)

(52) U.S. Cl. .................. 356/445; 250/227.16
(58) Field of Classification Search ........... 252/301; 356/296, 445; 428/212; 264/1.6, 10; 435/6; 523/333
See application file for complete search history.

(56) References Cited

U.S. PATENT DOCUMENTS

| | | | |
|---|---|---|---|
| 4,101,698 A | 7/1978 | Dunning et al. | |
| 4,340,276 A | 7/1982 | Maffitt et al. | |
| 4,618,525 A | 10/1986 | Chamberlain et al. | |
| 4,871,790 A | 10/1989 | Lamanna et al. | |
| 5,026,599 A | 6/1991 | Koskenmaki | |
| 5,030,669 A | 7/1991 | Hendrickson et al. | |
| 5,178,726 A | 1/1993 | Yu et al. | |
| 5,238,623 A | 8/1993 | Mrozinski | |
| 5,330,855 A | 7/1994 | Semancik et al. | |
| 5,366,140 A | 11/1994 | Koskenmaki et al. | |
| 5,514,728 A | 5/1996 | Lamanna et al. | |
| 5,611,998 A | 3/1997 | Aussenegg et al. | |
| 5,618,475 A | 4/1997 | Johnson et al. | |
| 5,665,277 A | 9/1997 | Johnson et al. | |
| 5,736,073 A | 4/1998 | Wadley et al. | |
| 5,750,641 A | 5/1998 | Ezzell et al. | |
| 5,774,619 A * | 6/1998 | Bruesselbach | 385/137 |
| 5,976,678 A | 11/1999 | Kawazu et al. | |

(Continued)

FOREIGN PATENT DOCUMENTS

EP    1 130 051 A2    9/2001

(Continued)

OTHER PUBLICATIONS

Raether, "Surface Plasmons on Smooth and Rough Surfaces and on Graphics", Springer Tracts in Modern Physics, (1988), vol. 111, Springer-Verlag, Berlin Heidelberg, New York.

(Continued)

*Primary Examiner*—Gregory J. Toatley, Jr.
*Assistant Examiner*—Jarreas Underwood
(74) *Attorney, Agent, or Firm*—Kent S. Kokko (57) ABSTRACT

The present invention is directed to an article comprising a thermoplastic polymer film and a discontinuous metallic nanoparticle coating, of an average size less than 100 nm, and the process for preparing the same. The coated film may be further stretched or shrunk to shift the absorbance peak maximum to the desired degree. The coating is formed by depositing a discontinuous layer of metallic nanoparticles by a physical vapor deposition method.

38 Claims, 6 Drawing Sheets

U.S. PATENT DOCUMENTS

| | | | |
|---|---|---|---|
| 6,025,202 | A | 2/2000 | Natan |
| 6,242,264 | B1 | 6/2001 | Natan et al. |
| 6,344,272 | B1 | 2/2002 | Oldenburg et al. |
| 6,411,748 | B1* | 6/2002 | Foltzer .......................... 385/7 |
| 6,458,431 | B2 | 10/2002 | Hill et al. |
| 6,569,517 | B1 | 5/2003 | McGurran et al. |
| 6,579,721 | B1 | 6/2003 | Natan et al. |
| 6,579,726 | B1 | 6/2003 | Natan et al. |
| 6,592,945 | B2* | 7/2003 | Suzuki et al. ................ 427/387 |
| 6,641,921 | B2 | 11/2003 | Falaas et al. |
| 6,642,295 | B2* | 11/2003 | Border et al. ................ 524/437 |
| 6,686,308 | B2 | 2/2004 | Mao et al. |
| 6,689,190 | B2 | 2/2004 | Pozarnsky |
| 6,689,192 | B1 | 2/2004 | Phillips et al. |
| 6,723,388 | B2 | 4/2004 | Svendsen et al. |
| 6,770,337 | B2 | 8/2004 | Debe et al. |
| 6,773,926 | B1* | 8/2004 | Freund et al. ............... 436/149 |
| 6,778,316 | B2 | 8/2004 | Halas et al. |
| 6,783,349 | B2 | 8/2004 | Neavin et al. |
| 6,808,658 | B2 | 10/2004 | Stover |
| 6,827,886 | B2 | 12/2004 | Neavin et al. |
| 6,828,786 | B2 | 12/2004 | Scherer et al. |
| 6,830,713 | B2 | 12/2004 | Hebrink et al. |
| 6,838,486 | B2* | 1/2005 | Ryang ......................... 516/90 |
| 6,846,638 | B2 | 1/2005 | Shipwash |
| 6,875,465 | B2* | 4/2005 | Bishop et al. ................. 516/90 |
| 7,002,697 | B2* | 2/2006 | Domash et al. ............. 356/519 |
| 7,030,989 | B2* | 4/2006 | Yager et al. ................. 356/445 |
| 2002/0090507 | A1 | 7/2002 | Barth et al. |
| 2002/0142306 | A1 | 10/2002 | Coleman et al. |
| 2002/0145792 | A1* | 10/2002 | Jacobson et al. ........... 359/296 |
| 2003/0118729 | A1 | 6/2003 | Bishop et al. |
| 2003/0129545 | A1 | 7/2003 | Kik et al. |
| 2003/0145681 | A1 | 8/2003 | El-Shall et al. |
| 2003/0157732 | A1 | 8/2003 | Baker et al. |
| 2003/0165680 | A1* | 9/2003 | Brady et al. ................ 428/402 |
| 2003/0170687 | A1* | 9/2003 | Chilkoti et al. ................ 435/6 |
| 2003/0203222 | A1* | 10/2003 | Philips et al. ............... 428/472 |
| 2004/0038386 | A1 | 2/2004 | Zesch et al. |
| 2004/0101454 | A1 | 5/2004 | Johnson et al. |
| 2004/0126649 | A1 | 7/2004 | Chen et al. |
| 2004/0131799 | A1* | 7/2004 | Arsenault et al. .......... 428/1.26 |
| 2004/0157237 | A1 | 8/2004 | Malak et al. |
| 2004/0197595 | A1 | 10/2004 | Callenbach et al. |
| 2004/0218184 | A1 | 11/2004 | Jorgenson et al. |
| 2004/0253138 | A1 | 12/2004 | Malak |
| 2005/0003520 | A1 | 1/2005 | Misiakos et al. |
| 2005/0136638 | A1 | 6/2005 | Voss-Kehl et al. |

FOREIGN PATENT DOCUMENTS

| | | |
|---|---|---|
| EP | 1 300 435 A1 | 4/2003 |
| WO | WO97/43042 | 11/1997 |
| WO | WO98/10289 A1 | 3/1998 |
| WO | WO99/05315 A2 | 2/1999 |
| WO | WO99/19066 | 4/1999 |
| WO | WO 00/06495 | 2/2000 |
| WO | WO 00/34033 A1 | 6/2000 |
| WO | WO 03/093809 A1 | 11/2003 |
| WO | WO 2004/000491 A2 | 12/2003 |
| WO | WO 2004/044232 A1 | 5/2004 |
| WO | WO 2004/092439 A2 | 10/2004 |
| WO | WO 2005/008243 A1 | 1/2005 |

OTHER PUBLICATIONS

Kerker, "The Scattering of Light", (1969), pp. 198-217, Academic Press, Inc., New York.

Seraphin, "Spectrally Selective Surfaces and Their Impact on Photothermal Solar Energy Conversion", Ch. 2 of "Solar Energy Conversion: Solid-State Physics Aspects", (1979), pp. 5-55, vol. 31, Springer-Verlag, Berlin Heidelberg, New York.

Blackborow et al., "Metal Vapour Synthesis in Organometallic Chemistry", (1979), Springer-Verlag, Berlin Heidelberg, New York.

Hache et al., "The Optical Kerr Effect in Small Metal Particles and Metal Colloids: The Case of Gold", Applied Physics A Solids and Surfaces, (Dec. 1988), pp. 347-357, vol. A 47, No. 4.

Alfrey et al, "Physical Optics of Iridescent Multilayered Plastic Films", Polymer Engineering and Science, (Nov. 1969), pp. 400-404, vol. 9, No. 6, Society of Plastics Engineers, Inc.

Pockrand et al, "Excitation-Surface Plasmon Coupling: An Experimental Investigation", (Dec. 1982), pp. 6289-6295, Journal of Chemical Physics, vol. 77, No. 12, American Institute of Physics.

Yatsuya et al., "A New Technique for the Preparation of Extremely Fine Metal Particles", Japanese Journal of Applied Physics, (1974), pp. 749-750, vol. 13, Physical Society of Japan and the Japan Society of Applied Physics.

Jain et al., "Optical Properties of Silver Colloidal Centers in KCL Crystals", Journal of Physics and Chemistry of Solids, (1974), pp. 1231-1236, vol. 35, Pergamon Press.

Ruppin et al., "Phonon-Plasmon Modes in Small GaN Crystals", Journal of Physics and Chemistry of Solids, (1974), pp. 1311-1315, vol. 35, Pergamon Press.

Bohren, "How Can a Particle Absorb More Than the Light Incident on It?", American Journal of Physics, (Apr. 1983), pp. 323-327, vol. 51, No. 4, American Institute of Physics, New York, NY.

Montali et al., "Polarizing Energy Transfer in Photoluminescent Materials for Display Applications", Nature, (Mar. 1998), pp. 261-264, vol. 392, No. 6673, Macmillan Magazines Ltd.

Holland, "Vacuum Deposition of Thin Films", (1956), John Wiley & Sons Inc., NY.

Palik, "Handbook of Optical Constants of Solids III", Institute for Physical Science and Technology, (1998), Academic Press, San Diego, CA.

Andres et al., "Self-Assembly of a Two-Dimensional Superlattice of Molecularly Linked Metal Clusters", Science, (Sep. 1996), pp. 1690-1693, vol. 273, American Association for the Advancement of Science, Washington, DC.

Carlotto, "The Chemistry of Thin Film Color", Society of Vacuum Coaters, (Apr. 15-20, 2000), pp. 58-60, 43rd Annual Technical Conference Proceedings.

Hessel et al., "A New Theory of Wood's Anomalies on Optical Gratings", Appplied Optics, (Oct. 1965), pp. 1275-1297, vol. 4, No. 10.

Oldenburg et al., "Light Scattering from Dipole and Quadrupole Nanoshell Antennas", Applied Physics Letters, (Aug. 1999), pp. 1063-1065, vol. 75, No. 8, American Institute of Physics.

Hale et al., "Enhancing the Active Lifetime of Luminescent Semiconducting Polymers via Doping with Metal Nanoshells", Applied Physics Letters, (Mar. 2001), pp. 1502-1504, vol. 78, No. 11, American Institute of Physics.

Wiesner et al., "Anisometric Gold Colloids. Preparation, Characterization, and Optical Properties", Chemical Physics Letters, (May 1989), pp. 569-575, vol. 157, No. 6, Elsevier Science Publishers B.V.

Strelow et al., "Chemisorptionof Phosphine on Colloidal Silver in Aqueous Solution", Journal of Physical Chemistry, (1994), pp. 3032-3035, vol. 98, No. 11, American Chemical Society.

Lazarides et al., "DNA-Linked Metal Nanosphere Materials: Structural Basis for the Optical Properties", Journal of Physical Chemistry B, (2000), pp. 460-467, vol. 104, No. 3, American Chemical Society.

Chang et al., "The Shape Transition of Gold Nanorods", Langmuir, (1999), pp. 701-709, vol. 15, No. 3, American Chemical Society.

Averitt et al., "Linear Optical Properties of Gold Nanoshells", Journal of Optical Society of America B, (Oct. 1999), pp. 1824-1832, vol. 16, No. 10, Optical Society of America.

Averitt et al., "Ultrafast Optical Properties of Gold Nanoshells", Journal of Optical Society of America B, (Oct. 1999), pp. 1814-1823, vol. 16, No. 10, Optical Society of America.

Thio et al., "Surface-Plasmon-Enhanced Transmission Through Hole Arrays in Cr Films", Journal of Optical Society of America B, (Oct. 1999), pp. 1743-1748, vol. 16, No. 10, Optical Society of America.

Liao et al., "Surface-Enhanced Raman Scattering on Gold and Aluminum Particle Arrays", Optics Letters, (Oct. 1982), pp. 483-485, vol. 7, No. 10, Optical Society of America.

Doyle, "Absorption of Light by Colloids in Alkali Halide Crystals", Physical Review, (Aug. 1958), pp. 1067-1072, vol. 111, No. 4.

Granqvist et al., "Optical Properties of Ultrafine Gold Particles", Physical Review B, (Oct. 1977), pp. 3513-3534, vol. 16, No. 8.

Johnson et al., "Optical Constants of the Noble Metals", Physical Review B, (Dec. 1972), pp. 4370-4379, vol. 6, No. 12.

Sobnack et al., "Stationary Surface Plasmons on a Zero-Order Metal Grating", Physical Review Letters, (Jun. 1998), pp. 5667-5670, vol. 80, No. 25, American Physical Society.

Stuart et al. "Enhanced Dipole-Dipole Interaction Elementary Radiators Near a Surface", Physical Review Letters, (Jun. 1998), pp. 5663-5666, vol. 80, No. 25.

Rowe et al., "Ultrahigh-Vacuum Studies of Enhanced Raman Scattering from Pyridine on Ag Surfaces", Physical Review Letters, (Jun. 1980), pp. 1770-1773, vol. 44, No. 26.

Collier et al., "Reversible Tuning of Silver Quantum Dot Monolayers Through the Metal-Insulator Transition", Science, (Sep. 1997), pp. 1978-1981, vol. 277.

Quinten et al., "Optical Properties of Aggregates of Small Metal Particles", Surface Science, (1986), pp. 557-577, vol. 172, Elsevier Science Publishers B. V., North-Holland, Amsterdam.

Kreibig, "Optical Absorption of Small Metallic Particles", Surface Science, (1985), pp. 678-700, vol. 156, Elsevier Science Publishers B. V., North-Holland, Amsterdam.

Foss et al., "Template-Synthesized Nanoscopic Gold Particles: Optical Spectra and the Effects of Particle Size and Shape", Journal of Physical Chemistry, (1994), pp. 2963-2971, vol. 98, No. 11, American Chemical Society.

Perenboom et al., "Electronic Properties of Small Metallic Particles", Physics Reports (Review Section of Physics Letters), (1981), pp. 173-292, vol. 78, No. 2, North-Holland Publishing Company.

Kamat, "Photophysical, Photochemical and Photocatalytic Aspects of Metal Nanoparticles", Journal of Physical Chemistry B, (2002), pp. 7729-7744, vol. 106, No. 32, American Chemical Society.

Raveendran et al., "Completely "Green" Synthesis and Stabilization of Metal Nanoparticles", Journal of American Chemical Society, (2003), pp. 13940-13941, vol. 125, No. 46, American Chemical Society.

Jensen et al., "Nanosphere Lithography: Tunable Localized Surface Plasmon Resonance Spectra of Silver Nanoparticles", Journal of Physical Chemistry B, (2000), pp. 10549-10556, vol. 104, No. 45, American Chemical Society.

Marshall et al., "A Silver-Free, Single-Sheet Imaging Medium Based on Acid Amplification", Science, (Aug. 2002), pp. 1516-1521, vol. 297.

Strelow et al., "Chemisorption of Phosphine on Colloidal Silver in Aqueous Solution", Journal of Physical Chemistry, (1994), pp. 3032-3035, vol. 98, No. 11, American Chemical Society.

Biswas et al., "Polymer-Metal Optical Nanocomposites with Tunable Particle Plasmon Resonance Prepared by Vapor Phase Co-Deposition", Materials Letters, (2004), pp. 1530-1534, vol. 58, Elsevier B. V.

Lue et al., "A Review of Characterization and Physical Property Studies of Metallic Nanoparticles", Journal of Physics and Chemistry of Solids, (2001), pp. 1599-1612, vol. 62, Elsevier Science Ltd.

Chauhan et al., "Synthesis, Stabilization, and Applications of Nanoscopic Siloxane-Metal Particle Conjugates", Journal of Orgamo Metallic Chemistry, (2003), pp. 24-31, vol. 686, Elsevier B. V.

Kensuke et al., "In Situ Spectroscopic and Microscopic Study on Dispersion of Ag Nanoparticles in Polymer Thin Films", J. Phys. Chem. B., (2000), pp. 10168-10173, vol. 104, No. 44, American Chemical Society.

Zheng et al., "Optical Properties of Silver-Dispersed PVP Thin Film", Materials Research Bulletin, (2001), pp. 853-859, vol. 36, Elsevier Science Ltd.

Lu et al., "High-Density Silver Nanoparticle Film With Temperature-Controllable Interparticle Spacing for a Tunable Surface Enhanced Raman Scattering Substrate", Nano Letters, (2005), pp. 5-9, vol. 5, No. 1, American Chemical Society.

\* cited by examiner

THERMOPLASTIC FILM HAVING METALLIC NANOPARTICLE COATING

FIELD OF THE INVENTION

The present invention is directed to a metallic nanoparticle coated thermoplastic film and the process for preparing the same.

BACKGROUND

Metallic nanoparticles, having a diameter of about 1-100 nanometers (nm), are important materials for applications that include semiconductor technology, magnetic storage, electronics fabrication, and catalysis. Metallic nanoparticles have been produced by gas evaporation; by evaporation in a flowing gas stream; by mechanical attrition; by sputtering; by electron beam evaporation; by thermal evaporation; by electron beam induced atomization of binary metal azides; by expansion of metal vapor in a supersonic free jet; by inverse micelle techniques; by laser ablation; by laser-induced breakdown of organometallic compounds; by pyrolysis of organometallic compounds; by microwave plasma decomposition of organometallic compounds, and by other methods.

It is known that metallic nanoparticles possess unique optical properties. In particular, metallic nanoparticles display a pronounced optical resonance. This so-called plasmon resonance is due to the collective coupling of the conduction electrons in the metal sphere to the incident electromagnetic field. This resonance can be dominated by absorption or scattering depending on the radius of the nanoparticle with respect to the wavelength of the incident electromagnetic radiation. Associated with this plasmon resonance is a strong local field enhancement in the interior of the metal nanoparticle. A variety of potentially useful devices can be fabricated to take advantage of these specific optical properties. For example, optical filters or chemical sensors based on surface enhanced Raman scattering (SERS) have been fabricated.

U.S. Pat. No. 6,344,272 (Oldenburg et al.) describes nanoparticles comprised of a nonconducting inner layer that is surrounded by an electrically conducting material. The ratio of the thickness of the nonconducting layer to the thickness of the outer conducting shell is determinative of the wavelength of maximum absorbance or scattering of the particle. The reference notes that a serious practical limitation to realizing many applications of solid metal nanoparticles is the inability to position the plasmon resonance at desired wavelengths. For example, solid gold nanoparticles of 10 nm in diameter have a plasmon resonance centered at 520 nm. This plasmon resonance cannot be controllably shifted by more than approximately 30 nanometers by varying the particle diameter or the specific embedding medium.

Surface Plasmon Resonance (SPR) is the resonant excitation of oscillating free charges at the interface of a metal and a dielectric. When SPR spectra are generated and collected, they can be used to determine specificity, kinetics, affinity, and concentration with respect to the interactions between two or more molecules, where one of the molecules is attached to a solid sensing surface. Reaction kinetics corresponds to both an association and a dissociation rate at which an analyte interacts with the bound detection molecule. Affinity refers to the strength with which an analyte binds to the detecting molecule. Specificity refers to the propensity of a molecule to bind to the detecting molecule to the exclusion of other molecules. SPR spectra have been used in studies involving many types of molecules including proteins, peptides, nucleic acids, carbohydrates, lipids, and low molecular weight substances (e.g., hormones and pharmaceuticals).

Recently, sensor devices have been developed in the known art to exploit the unique optical properties of these nanoparticles. SPR measurements have been made using gold nanoparticle suspensions to detect biomolecular interactions in real time by monitoring the absorbance of colloidal suspensions.

One analytical technique, known as SPR based bio-sensing, has been developed to enable direct measurements of the association of ligands with receptors, without the use of indirect labels, such as fluorescent markers and radioactive molecular tags. This label free direct sensing technique reduces the time and workload required to perform assays, and minimizes the risk of producing misleading results caused by molecular changes induced by the use of indirect labels. Another important aspect of the bio-sensing technique is that SPR based bio-sensing enables bio-molecular interactions to be measured continuously and in real-time, thereby enabling the determination of association and dissociation kinetic data in contrast to traditional "end point" analytical methods.

Over the past decade, interest in the unique optical properties of metallic nanoparticles has increased considerably with respect to the use of suspensions and films incorporating these nanoparticles for the purposes of exciting surface plasmons to enable the detection of SPR spectra. In addition, Surface Enhanced Raman Spectroscopy (SERS) for infrared absorbance spectral information and surface enhanced fluorescence for enhanced fluorescence stimulation can also be detected. Nanoparticles are particles that are less than 100 nanometers in diameter. Metallic nanoparticles display large absorbance bands in the visible wavelength spectrum yielding colorful colloidal suspensions. The physical origin of the light absorbance is due to incident light energy coupling to a coherent oscillation of the conduction band electrons on the metallic nanoparticle. This coupling of incident light is unique to discrete nanoparticles and films formed of nanoparticles (referred to as metallic island films). Achieving SPR with ordinary bulk materials requires the use of a prism, grating, or optical fiber to increase the horizontal component of the incident light wave vector (i.e., to achieve the required coupling).

SUMMARY

Methods and materials are needed that can be used to shift the wavelength of maximum absorption of metallic nanoparticles. Methods for producing materials having defined wavelength absorbance peak maximum across the visible and infrared range of the electromagnetic spectrum are needed. By 'metallic" it is meant elemental metals and compounds thereof.

The present invention overcomes limitations of the prior art by providing a thermoplastic film having a metallic nanoparticle coating wherein the plasmon resonance absorbance spectrum may be shifted by orientation (stretching) or shrinking of the coated film. The article of the present invention could be used in such diverse applications as optical switching devices, optical communication systems, infrared detectors, infrared cloaking devices, chemical sensors, passive solar radiation collection or deflecting devices and the like. The ability to shift the absorption spectrum is surprising in view of nanoparticle solutions, where increasing or decreasing the concentration (and the interparticle distance) may increase or decrease the intensity of the absorption spectrum, but does not shift the absorption peak maximum. The intensity of the absorption spectrum may also be increased by providing a multilayer article comprising two or more layers of the nanoparticle coated films.

In one embodiment the invention provides a method of preparing a nanoparticle coated thermoplastic film surface comprising the steps of providing a thermoplastic film, depositing a discontinuous coating of metallic nanoparticle on the surface of the film by physical vapor deposition, and stretching the coated film, to provide an article having a predetermined absorption spectrum. The method may further comprise the step of shrinking the stretched, nanoparticle-coated article.

In another embodiment, the invention provides an optical article exhibiting surface plasmon resonance comprising the metallic nanoparticle-coated thermoplastic film, wherein the absorption peak maximum may be adjusted by stretching (e.g. orientation) or shrinking of the article. The light at a certain wavelength and certain angle will enter in resonance with the surface plasmons and the photon will be absorbed. This is seen by a maximum in the absorbance spectra. The absorption spectrum is a function of the degree of stretching or shrinking, the nature of the metal, the size of the nanoparticles, the average coating thickness, and the dielectric constant of the thermoplastic film layer.

In another embodiment the invention provides a sensor comprising the metallic nanoparticle coated thermoplastic film, wherein a binding agent disposed over at least a portion of said metallic nanoparticle and wherein said binding agent interacts with a predetermined substance present in said biological, biochemical, chemical or environmental sample.

Various features, embodiments and advantages of the invention will be apparent from the following detailed description of the invention and the claims. The above summary is not intended to describe each illustrated embodiment or every implementation of the present disclosure. The detailed description that follows more particularly exemplifies certain preferred embodiments utilizing the principles disclosed herein.

DETAILED DESCRIPTION

The present invention is directed, in part, to methods of forming a nanoparticle coating on an stretched thermoplastic polymer film. The methods include providing a thermoplastic polymer film, onto which is deposited a discontinuous coating of metallic nanoparticles of an average size less than 100 nm by physical vapor deposition. The coated film may be further stretched or shrunk to shift the absorbance peak maximum to the desired degree.

The invention is further directed to an article comprising a thermoplastic polymer film substrate and a discontinuous metallic nanoparticle coating on the thermoplastic polymer film. The coating is formed by depositing a discontinuous layer of metallic nanoparticles by a physical vapor deposition method. The majority of the metal nanoparticles are usually elemental metal nanoparticles, although other metallic nanoparticle such as oxides are also contemplated.

As used herein, "discontinuous" means the nanoparticle coating is disposed as islands of nanoparticles or agglomerates thereof, surrounded by uncoated areas, such that the coating exhibits surface plasmon resonance. Continuous coatings, regardless of thickness, do not yield surface plasmon resonance.

The present invention provides a metallic nanoparticle coating on a thermoplastic polymeric film, the nanoparticles having a mean number average particle diameter in the range of 1 to 100 nanometers and most preferably 1 to 50 nanometers. The coating generally has an average thickness is less than 100 nm, preferably less than 10 nm. The nanoparticles may be substantially spherical, but in some cases are elongated, having an aspect ratio (length to diameter) of greater than 1.5:1 (i.e. are substantially oblong). Optionally, the film is stretched (oriented) prior to deposition, and may subsequently be further stretched or shrunk to shift the absorbance peak maximum to the desired degree.

Average thickness of the nanoparticle coating may be measured during deposition using a commercially available quartz crystal microbalance. After deposition a number of chemical assays can be used to characterize the quantity of metal in any specified area. Particle diameter (formed by agglomeration of the nanoparticles) is typically measured using light scattering techniques known in the art. Primary particle diameter is typically measured using transmission electron microscopy or atomic force microscopy.

The coated article allows the optical properties to by varied by stretching or shrinking. As the article is stretched or shrunk, the absorbance spectrum maximum is shifted to shorter or longer wavelengths respectively, so the optical properties may be varied as desired. In optical filter applications, this enables one to adjust the absorbance to a preselected maximum, so as to most efficiently filter out undesired wavelengths such as UV or IR wavelengths. In sensor applications, it allows one to match the absorbance peak maximum to a particular analyte and thereby maximize the response signal.

The nanoparticles are prepared by physical vapor deposition techniques that generate the nanoparticles. Metal is heated under reduced pressure until vaporization occurs. Optionally, the metal vaporizes in the presence of a gas stream wherein the gas preferably is inert (nonreactive), although any gas that does not react with the metal may be used. The nanoparticles are transported or directed to a polymeric film (optionally by the gas stream) and deposited by impinging the metallic vapor onto the film, wherein nucleation and nanoparticle growth occurs. Generally in the absence of a gas stream the physical vapor deposition technique produces a metallic vapor than directly nucleates on the thermoplastic film surface. In the presence of a gas, the metallic vapor undergoes some degree of homogenous nucleation in the stream to produce the nanoparticles, which are deposited on the film surface.

The coating may be prepared by a method comprising the steps:
 a) vaporizing a metal, optionally in the presence of a nonreactive gas stream, to provide metallic vapor,
 b) optionally providing a second reactive gas capable of reacting with the metallic vapor (or metallic nanoparticles formed in the metallic vapor), and reacting the reactive gas with the metallic vapor (or metallic nanoparticles) to convert the same to metal oxide nanoparticles, and c) impinging the metallic vapor onto the film, wherein nucleation and growth of the nanoparticles occurs, to provide a nanoparticle coating thereon.

The deposition of the metallic nanoparticles on the thermoplastic polymeric film may be achieved using one of several physical vapor deposition techniques known to those of ordinary skill in the art. Such processes include vapor deposition, cathode sputtering, pyrolysis, ion plating, e-beam deposition, and the like. Vapor deposition and cathode sputtering are often preferred in view of the uniformity of structure and thickness that can be obtained. Reference is made to Vacuum Deposition of Thin Films, L. Holland, 1970, Chapman and Hall, London, England with regard to the many available means of providing metal vapors and vapor coating techniques. If desired, the nanoparticle layer may be pattern coated by means of a mask, so that the metallic nanoparticle surface may be patterned.

Physical vapor deposition (PVD) processes involve the deposition of atoms, typically by evaporation or sputtering in a vacuum. PVD processes can be characterized by the steps of (1) generating a metallic vapor by evaporation or sputtering using resistance, induction, electron-beam heating, laser-beam ablation, direct current plasma generation, radio-frequency plasma generation, molecular beam epitaxy, or similar means; (2) transport of the metallic vapor from the source to the substrate by molecular flow, viscous flow, plasma gas transport, or the like; and (3) nanoparticle growth on the thermoplastic polymer film, wherein nucleation and growth of the nanoparticles occurs. With PVD a variety of substrate temperatures can be used to control the crystallization and growth mode of the material deposited, although generally the temperature of the thermoplastic polymer film is below the distortion temperature of the polymer.

To avoid deformation or melting of the film substrate during deposition, the film is generally maintained at a temperature at or below the distortion temperature of the polymer. The integrity of the film is maintained by controlling the deposition rate so that the temperature of the nanoparticles, or the heat released by the nanoparticles upon deposition (heat of condensation) does not lead to thermal deformation of the film. Generally, the temperature of the film is maintained at ambient conditions of the deposition chamber, and no special cooling of the film is required.

In a preferred embodiment, the nanoparticle coatings are applied to the thermoplastic polymer film by electron beam evaporation. This technique is based on heat production by high-energy electron beam bombardment on the metal to be deposited. The electron beam is generated by an electron gun, which uses the thermionic emission of electrons produced by an incandescent filament (cathode). Emitted electrons are accelerated towards an anode by a high difference of potential (kilovolts). The crucible (containing the source metal) itself or a near perforated disc can act as the anode. A magnetic field is often applied to bend the electron trajectory, allowing the electron gun to be positioned below the evaporation line. As electrons can be focused, it is possible to obtain a very localized heating on the metallic material to evaporate, with a high density of evaporation power (several kW). This allows control of the evaporation rate, from low to very high values. Cooling the crucible avoids contamination problems from heating and degasification.

Physical vapor deposition by sputtering is accomplished in a partial vacuum (between 13.3 to 1.33 Pa for a diode system and between 1.3 to 0.13 Pa for a magnetron system) when the target (usually a cathode) is bombarded with gas ions propelled by an electric field. The sputtering gas is typically a noble gas such as argon but the sputtering gas could include reactive elements that can be incorporated into the deposited film such as the deposition of nitrides, oxides and carbides. When the sputtering gas is ionized a glow discharge or plasma is produced. The gas ions are accelerated towards the target by an electric or electric and magnetic fields. Atoms from the target are ejected by momentum transfer and move across the vacuum chamber to be deposited on the substrate (the thermoplastic polymer film).

In another embodiment, the nanoparticle coatings are applied to the thermoplastic polymer film by sputter deposition. The sputtering apparatus generally consists of a three-source magnetron sputtering system arranged around the outer circumference of a cylindrical chamber containing a 38 cm (15 inch) diameter rotating drum. The substrates were mounted on the drum and rotated sequentially past positions in front of the sputtering sources at rates of between 1 and 8 rpm. The sources are shielded such that the sample is not coated from any two fluxes at the same time. The rate of material deposition and speed of rotation of the substrate in front of the targets determines the individual layer thicknesses comprising the final catalyst particles. Any vacuum pump that can draw a sufficient vacuum may be used. One such vacuum pump is a Varian AV8 cryopump (Varian Associates, Lexington, Mass.), which can be used in conjunction with an Alcatel 2012A rotary vane-roughing pump (Alcatel Vacuum Products, Hingham, Mass.). The cryopump may be partially isolated from the chamber by a butterfly valve. During deposition pressure may be maintained at 0.28 Pa (2.1 millitorr) as the sputtering gas flow rate was controlled by MKS flow controllers (MKS Instruments Inc., Andover, Mass.). Any inert or reactive sputtering gases may be used. Preferably either argon or an argon, oxygen mix is used. Control of the oxygen stoichiometry can be achieved by varying the argon/oxygen flow ratio. Any appropriate targets and power sources may be used. In one embodiment, an Advanced Energy MDX 500 power supply (Advanced Energy Industries, Inc., Fort Collins, Colo.) is used in the constant power mode of the power supply.

Useful metals that may be used in the physical vapor deposition step include, for example, Li, Na, K, Rb, Cs, Fr, Be, Mg, Ca, Sr, Ba, Ra, Y, La, Ac, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Al, In, TI, Sn, Pb, mixtures, oxides and alloys of these metals and even the lanthanides and actinides, if desired. Metals may be deposited sequentially or simultaneously.

Particularly useful metals are gold, aluminum, copper, iron, platinum, palladium, iridium, rhodium, osmium, ruthenium, titanium, cobalt, vanadium, magnesium, silver, zinc, and cadmium, indium, lanthanum, indium tin oxide (ITO) and antimony tin oxide (ATO), antimony indium tin oxide (AITO), tin, indium, lanthanum, boron, lanthanum hexaboride, rare earth metals and mixtures and alloys thereof, and mixtures and alloys thereof. Most preferred are the noble metals. Other metals are apparent to those skilled in the art.

The process may involve evaporation of the elemental metal itself, as with Au or Ag, or may involve evaporation of a precursor form with generation of the actual elemental metal taking place during the transport stage prior to contacting the polymeric film. An example would be evaporation of silver metal using argon as a nonreactive gas with subsequent exposure of the silver nanoparticles to a reactive oxygen environment, thereby forming ultrafine silver oxide coated nanoparticles (the particle core being silver) prior to contacting the polymeric film. Since the reactive gas is introduced at a site remote from the vaporization source after the nanoparticles have formed, the final nanoparticles consist of a central core and an outer shell, where the central core can be metal and where the outer shell can be comprised of a layer formed by reaction of the reactive gas with the metal nanoparticles.

Where used, the inert gas is generally selected from He, Ne, Ar, Xe, and $N_2$. Mixtures of two or more nonreactive gases can also be used. When modification of the metal is desired, a reactive gas can be introduced through a gas inlet that is positioned so as to minimize reaction with the bulk material in the crucible and allow thorough mixing of the reactive gas with the particles entrained in the gas stream, thereby allowing reaction with the particles to occur. The reactive and nonreactive gases generally are at room temperature but the temperature can be elevated or reduced as desired. The term reactive includes 1) direct reaction with the particles, as in the case of metals, for example, with $O_2$, NO, $NO_2$, $CO_2$, CO, $AsH_3$, $H_2S$, $H_2Se$, $NH_3$, trimethylchlorosilane, methylamine, ethylene oxide, water, HF, HCl, or $SO_2$, or combinations thereof, to form the corresponding oxides or other compounds; or 2) adsorption, in which a volatile substance is introduced in the gas prior to contacting the dispersing medium, but the substance is either not a liquid under normal conditions (atmospheric pressure and 25° C.), the substance is not miscible with the dispersing medium, or else the substance acts to protect the surface of the nanoparticles from the dispersing medium or additives within the dispersing medium. Typical substances that could be adsorbed include polymers such as poly(methylmethacrylate) and polystyrene.

A useful apparatus for coating of the nanoparticles comprises:
  a) a furnace connected to a collection vessel, the furnace containing a heating means (e.g., resistive, inductive, e-beam, infrared, laser, plasma jet) and adapted to contain at least a first and optionally a second gas inlet tube, said second tube being located downstream from said first tube, and a means (e.g., a pump such as a rotary oil pump, an oil diffusion pump, piston pump, a Roots™ blower, and a turbomolecular pump) for evacuating the furnace and collection vessel, the vessel containing a dispersing medium;
  b) means (e.g., a ceramic, or metal crucible or slab that can be preloaded with metal or which can be continuously or batch-wise fed during operation of the apparatus, or the electrodes can be the means) for introducing a metal into said furnace and evacuation thereof;
  c) optionally, means (e.g., a micro metering valve, electronic flow controller, or gas dispersing tube) for introducing through the first inlet tube a first, non-reactive gas stream into the furnace;
  d) means (e.g., energy input as by e-beam, infrared, laser, inductive, resistive, or plasma jet) for evaporating the metal nanoparticles into the first gas stream;
  e) means for allowing condensation of the vaporized metallic nanoparticles (e.g., decreasing the temperature, raising the pressure, changing the chemical nature of the nonreactive gas, controlling the length of the transfer tube, controlling the gas flow rate, or combinations thereof) in the first gas stream to produce a dispersion of nanoparticles into the first gas stream;
  f) optionally, means (e.g., a micro metering valve, electronic flow controller, or gas dispersing tube) for introducing into the furnace through the second inlet tube a second, reactive gas stream, to allow reaction with the metallic nanoparticles;
  g) means for impinging the nanoparticles onto the thermoplastic polymer film.

Other reactor designs to provide dispersions of the invention can be envisioned, including a rotary metal atom reactor such as described in Metal Vapour Synthesis in Organometallic Chemistry, J. R. Blackborow and D. Young, Springer-Verlag (New York), 1979 and a spinning disk assembly such as described in Jpn. J. Appl. Phys., 13, 749 (1974). Both types of reactors could be used to generate dispersions of organic pigments. In addition to resistive heating, other means of applying heat to the pigment or pigment precursor may be envisioned. These include laser heating, inductive heating, plasma jet, plasma arc discharge, and others known to those skilled in the art.

With the process of the invention, no milling or chemical reduction processes are required in order to achieve the fine particle sizes obtained in the final coating. The nanoparticles of the present invention exhibit useful optical properties as demonstrated by the tunable or controllable absorbance spectra.

Examples of thermoplastic polymers for use in the film include polyesters, polyurethanes, polyamides, polystyrene, polyimides, polyolefins, alkyd, fluoropolymers, liquid crystal polymers, melamine, urea formaldehyde, diallyl phthalate, epoxide, phenolic, polyvinyl chloride, ionomeric polymers, acrylics and silicone polymers. Processes for preparing the thermoplastic polymers are well known, and the invention is not limited to a polymer made with a particular catalyst or process. The thermoplastic polymer film may be a single or multi-layer polymer film.

For some embodiments, preferred thermoplastic polymers are poly(alpha)olefins. Poly(alpha)olefins can include the homo-, co- and terpolymers of aliphatic mono-alpha-olefins as they are generally recognized in the art. Usually, the monomers employed in making such poly(alpha)olefins contain about 2 to 10 carbon atoms per molecule, though higher molecular weight monomers sometimes are used as comonomers. The invention is applicable also to blends of the polymers and copolymers prepared mechanically or in situ. Examples of useful monomers that can be employed to prepare the thermoplastic polymers include ethylene, propylene, 1-butene, 1-pentene, 4-methyl-1-pentene, 1-hexene, and 1-octene, alone, or in admixture, or in sequential polymerization systems. Examples of preferred thermoplastic polymers include polyethylene, polypropylene, propylene/ethylene copolymers, polybutylene and blends thereof.

In other embodiments any polyester-containing polymer may be preferred. Useful polyester polymers include polymers having terephthalate or naphthalate comonomer units, for example, polyethylene naphthalate (PEN), polyethylene terephthalate (PET) and copolymers and blends thereof. Examples of other suitable polyester copolymers are provided in, for example, U.S. Pat. Nos. 6,827,886 (Liu et al.), 6,808,658 (Stover et al), 6,830,713 (Hebrink et al) and 6,783,349 (Liu et al), which are incorporated herein by reference. Other suitable polyester materials include polycarbonates, polyarylates, and other naphthalate and terephthalate-containing polymers, such as, for example, polybutylene naphthalate (PBN), polypropylene naphtahalate (PPN), and blends and copolymers of the above with each other or with non-polyester polymers.

To preserve the desirable optical and electronic properties of the nanoparticle—coated article, it is preferred that the thermoplastic polymer film contain substantially no particulate additives such as pigments, fillers, reinforcing agents. Such additives, when present, can adversely affect the absorbance, alter the dielectric properties of the thermoplastic film and increase light scattering. Generally, such additives, if present, are less than 1 wt. % of the thermoplastic polymer film.

However, in some embodiments is may be desirable for the nanoparticle coated article to further comprise a dye or pigment for sensitizing the metallic nanoparticles to a particular wavelength of incident light. Such sensitizers may be coated on the nanoparticle-coated article before or after stretching, rather than embedded or dispersed in the polymer matrix. Such sensitizers are normally used at less than 1 weight percent, relative to the weight of the metallic nanoparticles.

The thermoplastic polymer film may be stretched before or after deposition of the metallic nanoparticles. It will be understood however that whether the film is stretched or unstretched prior to nanoparticle deposition, the coated film may be subsequently stretched (or shrunk) to provide the desired absorption spectrum. Thus a stretched film may be coated with nanoparticles, and then further stretched, or preferably an unstretched film is coated with nanoparticles, then stretched. Generally the stretch imparts a permanent deformation to the thermoplastic film so that the dimensions (length and/or width) are increased, although permanent deformation is not required for the desired effect.

The stretching increases (or shrinking decreases) the interparticle distance and shifts the absorbance peak maximum (to shorter or longer wavelengths respectively). In optical filter applications, this enables one to adjust the absorbance to a preselected maximum, so as to most efficiently filter out undesired wavelengths such as UV or IR wavelengths. In sensor applications, it allows one to match the absorbance peak maximum to a particular analyte and thereby maximize the response signal. Generally, the film is stretched (or shrunk) in an amount sufficient to shift the absorbance peak maximum of the coated article at least 10 nm, preferably at least 20 nm.

The polymer film may be stretched along one major axis (uniaxial), and may further be stretched along two major axes (biaxial). The stretching may be sequential or simultaneous. The degree of stretching is generally defined by the draw ratio, that is, the ratio of the final area to the original area. This stretching may be effected by a combination of techniques in the present invention, including the steps of calendering and length stretching. In general, the total draw ratio is at least 1.1x, and preferably at least 5x.

The conditions for stretching are chosen such that the desired shift in the absorption peak maximum is achieved and the integrity of the film is maintained. Thus when stretching in the machine and/or transverse directions, the temperature is chosen such that substantial tearing, distortion or fragmentation of the film is avoided and integrity is maintained. The film may be vulnerable to tearing or even catastrophic failure if the temperature is too low, or the stretching ratio(s) is/are excessively high. Preferably, the stretching temperature is above the glass transition temperature of the polymer. Such temperature conditions permit stretching in the X and Y directions without loss of film integrity.

When stretched, the core polymeric body may also be allowed to dimensionally relax in the cross-stretch direction from the natural reduction in cross-stretch (equal to the square root of the stretch ratio) or may also be constrained (i.e., no substantial change in cross-stretch dimensions). The core film may be stretched in the machine direction, as with a length orienter, and in the width direction using a tenter, or at diagonal angles.

It will be understood with respect to such stretching and orientation processes, that the pre-stretch temperature, stretch temperature, stretch rate, stretch ratio, heat set temperature, heat set time, heat set relaxation, and cross-stretch relaxation are selected to yield a film having desired properties, including a desired refractive index relationship.

If the stretching of the nanoparticle coated article is not equal in the transverse and longitudinal directions of the film, the article will exhibit different optical properties along the two major axes. This may result from uniaxial stretching, or from unequal biaxial stretching, where the stretching along one axis is greater than stretching along the other. It is preferred that the stretching is biaxial, and substantially equal on both axes, i.e. stretching along one axis is within 20% of stretching along the other axis.

If desired, the coated article may be annealed, preferably after stretching at a sufficient temperature to relieve stress but not so long or at so high a temperature that degradation of the film results. Suitable annealing temperatures vary with the type of polymer used. Preferably no pressure is applied to the film during the annealing step, only heat, although slight pressure less than about 10 psi is not detrimental. Ordinarily the film to be annealed is merely laid on a non-adherent support around which hot air is circulated or over which radiant heaters are placed.

The method may also comprise a step of shrinking the nanoparticle-coated film. Upon shrinking, the interparticle distance is reduced, and the absorbance peak maximum is shifted to longer wavelengths. In optical filter applications, this enables one to adjust the absorbance to a preselected maximum, so as to most efficiently filter out undesired wavelengths such as UV or IR wavelengths. In sensor applications, it allows one to match the absorbance peak maximum to a particular analyte and thereby maximize the response signal.

The present invention provides a shrinkable polymeric film, having a discontinuous metallic nanoparticle coating onto a portion of the polymeric film. The temperature of the shrinkable, coated polymeric film is elevated such that the projected surface area of the polymeric film shrinks by an amount sufficient that the absorbance peak maximum is shifted by at least 10 nm, preferably at least 20 nm. The step of shrinking may comprise exposing the shrinkable coated article to an elevated temperature for a time sufficient such that the article shrinks to less than 50 percent of its original projected surface area, sometimes less than 10 percent of its original projected surface area, and in certain embodiments less than 5 percent of its original projected surface area. During the shrinking step, it is advantageous to maintain the nanoparticle coated shrinkable film substantially flat to avoid uneven shrinkage, curling or other undesired deformation. The shrinkable film may be held in a tenter apparatus, or between two planar surfaces, during the heat shrinking.

In general, the nanoparticle-coated film is shrunk to provide the desired shift in the absorption spectrum. It should be recognized that excessive shrinking may lead to continuity between the previously discontinuous nanoparticles (and agglomerates), with an increase in electrical conductivity, reflection, and a loss or reduction in the surface plasmon resonance.

"Shrinkable," "shrinking" or "shrunk" shall mean, in the context of a material such as a substrate, that the material is capable of being, is, or has been decreased in its length in at least one dimension, whether by recovery, relaxation, or any other means. Percent shrinkage of the substrate is calculated using the following equation: percent shrinkage=100 percent×[pre-shrinking projected surface area—post-shrinking projected surface area]/pre-shrinking projected surface area. The nanoparticle coated polymeric shrink film substrate is typically shrunk using a heat source, such as by convection or contact heating. Also, in some implementations the heating process may be performed by microwave, radio frequency or infrared radiation.

If desired, the article may further comprise a protective layer for isolating the nanoparticles from environmental effects and mechanical stresses. The additional layer may be in contact with the metallic nanoparticle layer and the exposed surface of the thermoplastic film layer (i.e. the uncoated regions). This layer can act to reduce the surface roughness of both the polymeric layer and the overall construction, maintain the clarity and low haze of the article, and protect the nanoparticle layer from abrasion or oxidation. The protective layer may also be used to impart scratch resistance, chemical resistance and/or increased weatherability. The protective layer can be coextruded onto the surfaces of the coated surface of the thermoplastic film layer. Alternatively, the protective layer can be coated or laminated onto the thermoplastic film layer using a suitable pressure sensitive or non-pressure sensitive adhesive. Suitable coatings include, but are not limited to, hardcoats, adhesives, antistatics, adhesion promoting primers, UV stabilizing coating, friction reduction layers, etc. The protective layers are preferably made of a transparent polymer, for example, polyester (the same or different as that used in the construction of the thermoplastic polymer film layer.

The resulting article may be characterized as a stretchable or shrinkable film having a discontinuous coating of nanoparticles or agglomerates of nanoparticles on the surface thereof and that the article exhibits a surface plasmon resonance. The maximum average thickness of the coating is less than 100 nm, preferably less than 10 nm with areas of nanoparticles or agglomerates thereof and uncoated areas. Above approximately 100 nm the coating tends of behave as a continuous metalized film, which do not exhibit a surface plasmon resonance. If desired, a multilayer article comprised a plurality of nanoparticle coated films may be used. The films may be bonded or otherwise affixed to adjacent layers, or may comprise a stack of nanoparticle coated films. The multilayer articles increase the total absorbance (an additivity of absorbance) while maintaining the surface plasmon resonances, which is generally not possible by increasing the nanoparticle coating thickness. The multilayer article further shows an internal reflectance between layers, which results in an interference fringe.

The particles are partially fixed on the surface of the thermoplastic film and exposed, rather than embedded therein. Electron micrographs of a cross section of the coated article indicate the nanoparticles are substantially above the plane of the film. Generally more than 50%, typically more than 75% of the volume of the nanoparticles are above the surface. The particles remain fixed on the surface and are not easily removed. Typically less than 5% of the particles are removed by a tape test in which adhesive tape is affixed to the surface, and then peeled off at 180 degrees.

The nanoparticle coating used in the present invention avoids contamination of dispersed material due to the presence of milling media and the wear of mechanical parts; these problems having been noted above for dispersions prepared by conventional methods employing mechanical grinding of particulates. Additionally, no chemical reduction process is required in order to achieve the fine particle sizes obtained in the final coating; the solvents and reducing agents employed may contaminate the nanoparticles.

The absorption peak maximum of the coated article is a function of the metal or metallic compound deposited, the average thickness, the average particle size and shape (including agglomerates), the polymer used as the substrate and the degree of stretching (or shrinkage) of the article. As more metallic nanoparticles are deposited on the film and the average thickness increases, the absorption spectrum broadens and the maximum shifts to longer wavelengths. Electron micrographs reveal that as the mass thickness increases, the average particle size increases and the space (uncoated areas) between nanoparticles decreases as result of agglomeration. The average thickness may be controlled by the deposition rate and the time of deposition (the time the film is exposed to the metallic vapor). Several methods are available for characterizing the coating. The most common involves the mass thickness expressed as the average thickness of the nanoparticle coating.

The surface plasmon resonance and the absorption spectrum may be measure by spectrophotometry. As the absorption peak maximum of the spectrum shifts in response to stretching or shrinking, (or by controlling the aforementioned factors) the surface plasmon absorption spectrum of the metallic material may be measured by any suitable means for detection of transmitted light. Suitable means include UV-vis spectrophotometers, such as those available commercially from companies such as Beckman Coulter (DU Series 500 Scanning Spectrophotometers and DU Series 600 High Performance Spectrophotometers), Spectral Instruments (400 Series spectrometers), Varian Instruments (Cary 300Bio spectrophotometer), Safas Monaco (UVmc series spectrophotometers and D.E.S. spectrophotometers), Hitachi Instruments (U3010/3310 spectrophotometers) and others. Other means for detection of transmitted light include CCD cameras and flatbed optical scanners, which are also commercially available, such as a UMAX super vista S-12 flatbed scanner (UMAX Technologies, Inc.), preferably in combination with means for converting the image to grey scale and/or means for determining the density of an image, such as Scion Image software (Scion Corp).

The nanoparticle-coated article may be used as a sensor in analytical applications. The sensor comprises the nanoparticle coated thermoplastic film, and a binding agent disposed over at least a portion of the nanoparticle coating.

The binding agent interacts with a predetermined substance present in the biological, biochemical, chemical or environmental solution being tested with the sensor of the present invention. Any suitable reactive substance may be employed in the present invention, provided that it does not deleteriously affect either the metallic material or the optically transparent substrate.

According to certain preferred embodiments of the present invention, the binding agent is an agent involved in biological binding with at least one predetermined substance present in the biological, biochemical, chemical or environmental sample being tested. As used herein, the term "biological binding" is intended to mean the interaction between a corresponding pair of molecules that exhibit mutual affinity or binding capacity, typically specific or non-specific binding or interaction, including biochemical, physiological and/or pharmaceutical interactions, such as pairs of proteins, nucleic acids, glycoproteins, carbohydrates, hormones and the like. Illustrative examples of such corresponding pairs or molecules include, but are not limited to, the following: antibody/antigen; antibody/hapten; enzyme/substrate; enzyme/cofactor; enzyme/inhibitor; binding protein/substrate; carrier protein/substrate; lectin/carbohydrate; receptor/hormone; receptor/effector; nucleic acid strand/complementary nucleic acid strand; protein/nucleic acid repressor or inducer; ligand/cell surface receptor; and virus/ligand.

If desired, a functionalized material may be used to improve the adherence of the binding agent to the metallic nanoparticles and/or thermoplastic film layer. Accordingly, any material that adheres to both the metallic material and/or thermoplastic film layer, and the binding agent, but is not deleterious to either, may be employed as the second functionalized material. Suitable compounds for use as the second functionalized material are known to those skilled in the art and include, for example, organic compounds containing one or more of the functional groups including phosphonic acids, benzotriazoles, azlactones, —COOH, —CN, —NH$_2$, 2-pyridyl, —P(C$_6$H$_5$)$_2$ and/or —SH. Particularly preferred examples of a second functionalized material are carboxyl-terminated organothiols, such as 3-mercaptopropionic acid.

The choice of a particular functionalized material to be employed in such an embodiment of the present invention will therefore depend, at least in part, upon the particular metallic material and specific reactive substance employed. Accordingly, the choice of a particular second functionalized material may be determined empirically by one skilled in the art, in view of the particular metallic material and reactive substance being used.

When used as a sensor, it is preferred that the thermoplastic film layer be substantially transparent. As used herein, the term "substantially transparent" is intended to mean a substance that permits transmission of at least 50% of the light in the ultraviolet region (about 200 to about 400 nm), visible region (about 400 to about 750 nm), or infrared (greater than about 750 nm) of the spectrum.

The sensor(s) of the present invention are preferably employed in combination with a means for detection of transmitted light in the ultraviolet region (about 200 to about 400 nm), visible region (about 400 to about 750 nm) and/or infrared region (greater than about 750 nm) of the spectrum. Commercially available examples of such means for detection of transmitted light include, but are not limited to, UV-vis spectrophotometers, infrared spectrometers and flatbed optical scanners.

One preferred embodiment of the present invention is directed to a plurality of the sensors arranged in an array format. According to such an embodiment, an array of sensors is preferably employed in combination with a means for detection of transmitted light in the ultraviolet region (about 200 to about 400 nm) and/or visible region (about 400 to about 750 nm), such as a flatbed optical scanner or CCD camera, or the infrared region of the spectrum (greater than about 750 nm). Such an embodiment of the present invention is particularly useful for use in an endpoint-assay or as a screening tool in combinatorial chemistry, proteomics and/or genomics.

The present invention further provides an optical element for selective absorption and transmission of incident light, including polarized light. Advantageously, the absorption spectrum of the nanoparticle-coated article may be controlled by appropriate stretching or shrinking of the article. The optical film of the invention can be used in any application to provide selective absorption, transmission and reflection. The optical film can incorporate or be applied to other optical bodies or films to combine multiple optical effects. For example, the optical bodies can be incorporated along with one or more additional optically active layers to form an IR mirror, UV absorption construction, solar control construction, polarizer, or decorative construction. Similarly, the optical element of the invention can be used to provide optical filters to window glazing, and lenses made of glass or polycarbonates. The optical element may also find application in the construction of puncture or tear-resistant films, safety and security films, and as contrast enhancement layers for optical displays, for example, computer monitors, television screens, and the like.

EXAMPLES

These examples are merely for illustrative purposes only and are not meant to be limiting on the scope of the appended claims.

Example 1

Metallic nanoparticles were e-beam evaporated onto various films as follows: silver on biaxially oriented polystyrene (BOPS, refractive index of approximately 1.6), silver on biaxially oriented polypropylene (BOPP, refractive index of approximately 1.5), silver, then gold on biaxially oriented polypropylene (BOPP, refractive index of approximately 1.5), and gold on PFA (a copolymer of tetrafluoroethylene and perfluoromethylvinylether, available from Dyneon, St. Paul, Minn., refractive index of approximately 1.35).

These nanoparticle samples were made at an e-beam deposition rate of 2 Angstrom/second to yield a nominal average thickness of approximately 40 Angstrom.

Figure 6:
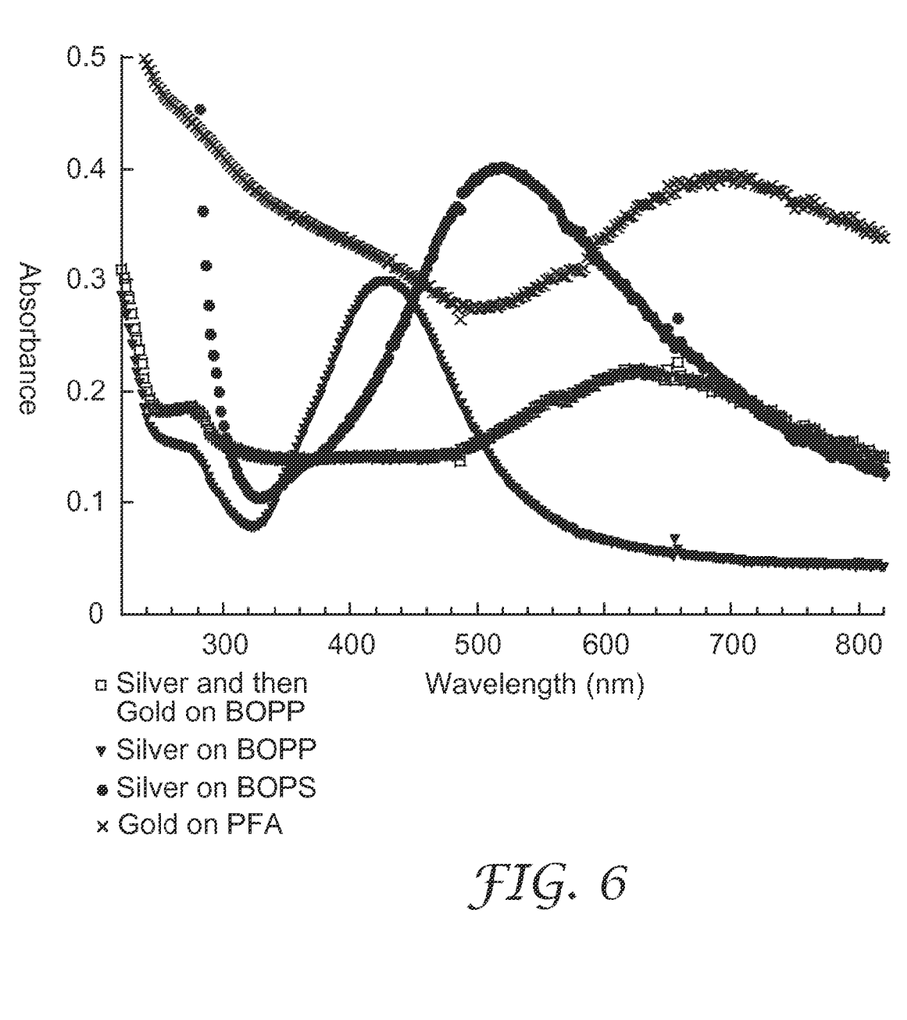
FIG. 6 are the absorbance spectra of Example 1.
Figure 7:
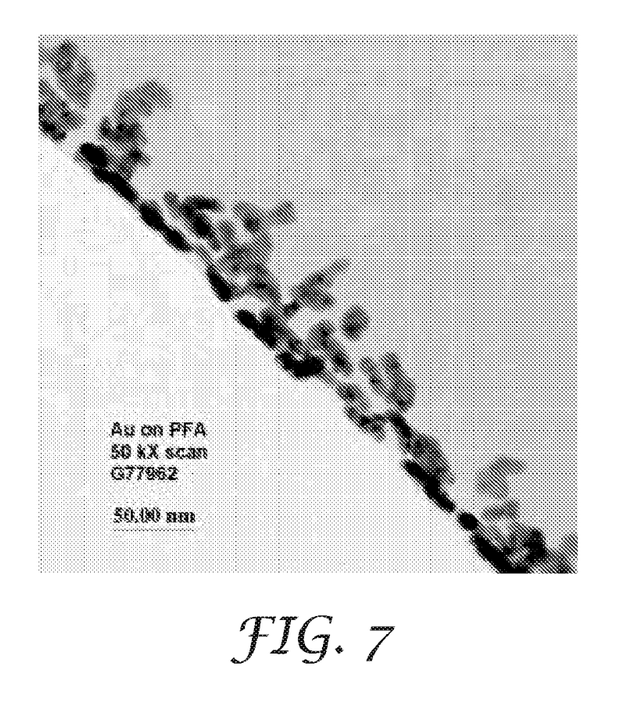
FIG. 7 is an electron micrograph of the gold nanoparticle coated PFA (tetrafluoroethylene-peerfluoromethyl vinyl ethyl copolymer) film of Example 1.

This example shows the effect of changing the refractive index of the substrate (compare Ag on PP vs Ag on PS) and the effect of sequentially coating two different metals (Au and Ag on PP). As result of the differing refractive indices of the polymer films coated with nanoparticles of similar size distributions, the films yielded different colors; the gold on PFA was a blue to light grey color, the silver on BOPS was a purple, and the silver on BOPP was amber yellow. The spectra showing the nanoparticle resonances of the coated articles are shown in FIG. 6. FIG. 6 also shows the shift in peak maxima obtained when a different refractive index substrate was utilized and also shows the effect of a sequential deposition of silver and then gold nanoparticles on a BOPP substrate. Absorption spectra were taken using a UV-Vis HP 8452A.Rev.A spectrophotometer. The sampling interval was 2 nanometers, the integration time was 0.5 seconds. The TEM micrograph of the gold/PFA sample is shown in FIG. 7. With regard to this sample, normally gold nanoparticles show an absorbance peak maximum of 500 to 530 nm. As can be seen in FIG. 6, this maximum is shifted to ~700 nm, and it is believed this is due to the non-spherical, oblong gold nanoparticles, as seen in FIG. 7, despite the lower refractive index of the polymer film.

Example 2

Figure 2:
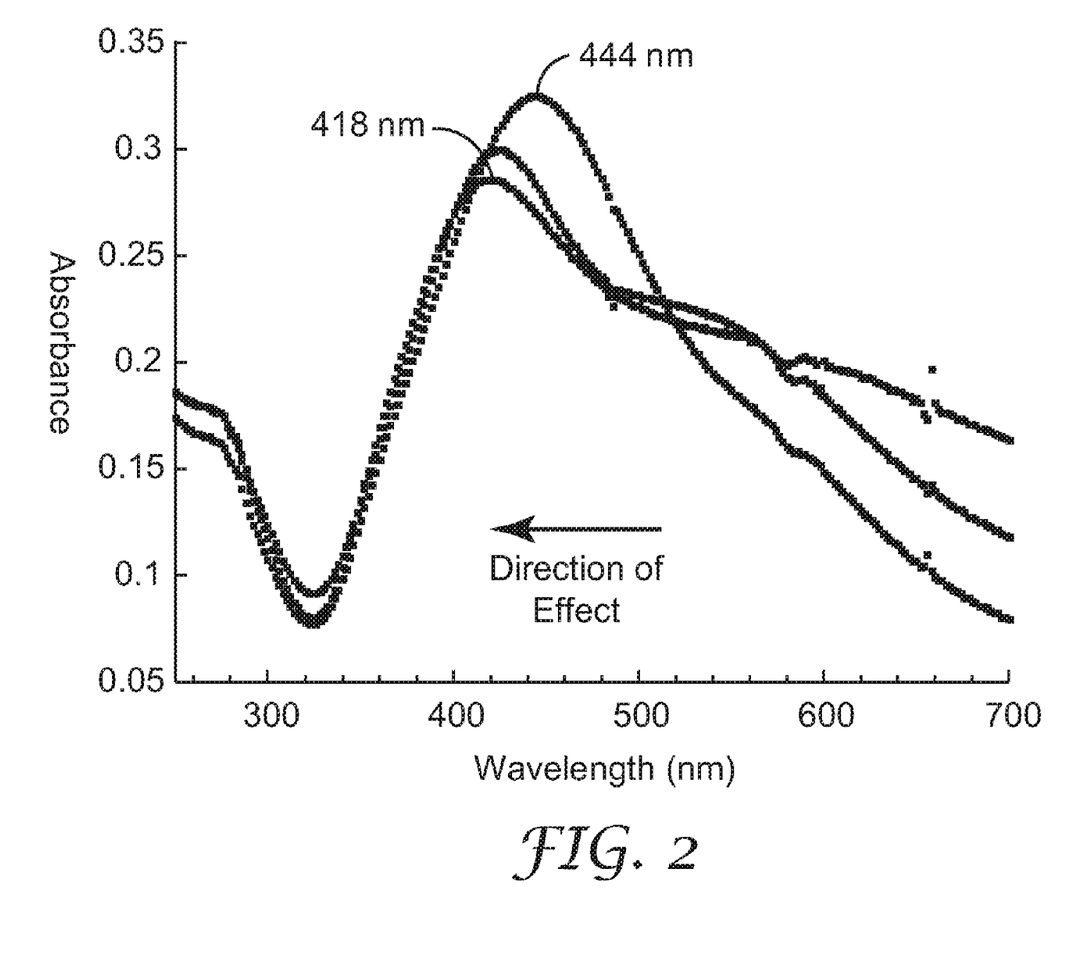
FIG. 2 is the absorbance spectra of Example 2.

Silver nanoparticles were e-beam evaporated onto biaxially oriented polypropylene (BOPP) film to yield a 60-Angstrom coating. The coated BOPP film had a yellowish/amber tint. Samples of the coated film were stretched in an Instron tensile testing machine (Model 1122 from Instron Corp.; Canton, Mass.) with a temperature conditioning chamber set at 100° C. and a stretching rate of 0.25 centimeters per minute (0.1 inches per minute). UV-Vis spectra were taken as described in Example 1 of the unstretched film, the film was stretched to 50% strain in 2 orthogonal directions, and the film stretched to 100% strain in one direction. The spectra are shown in FIG. 2.

The absorbance spectra reveal a second maximum, or shoulder, at approximately 540 to 580 nm as result of the orientation. As the coated film is oriented, the nanoparticle spacing in the direction of orientation becomes greater, and the absorbance peak maximum is shifted to shorter wavelengths. Concurrently, the nanoparticle distance in the direction perpendicular to the direction of orientation becomes smaller, and a new absorbance peak at higher wavelengths develops.

Example 3

Figure 1:
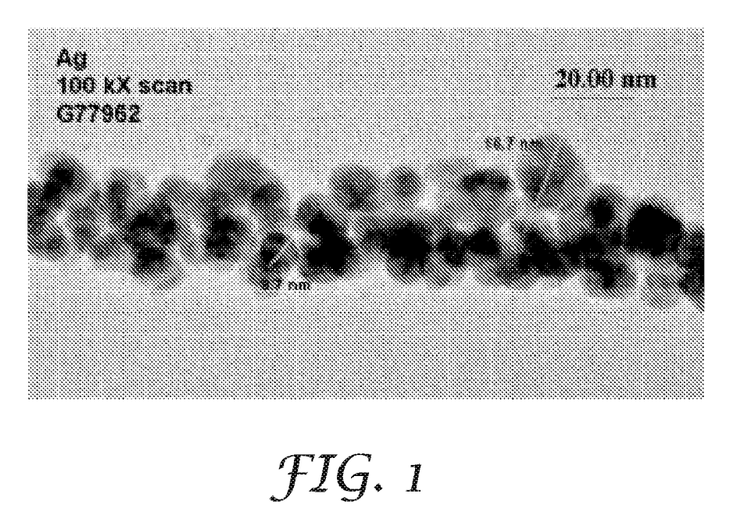
FIG. 1 is an electron micrograph of the coated film of Example 3.
Figure 3:
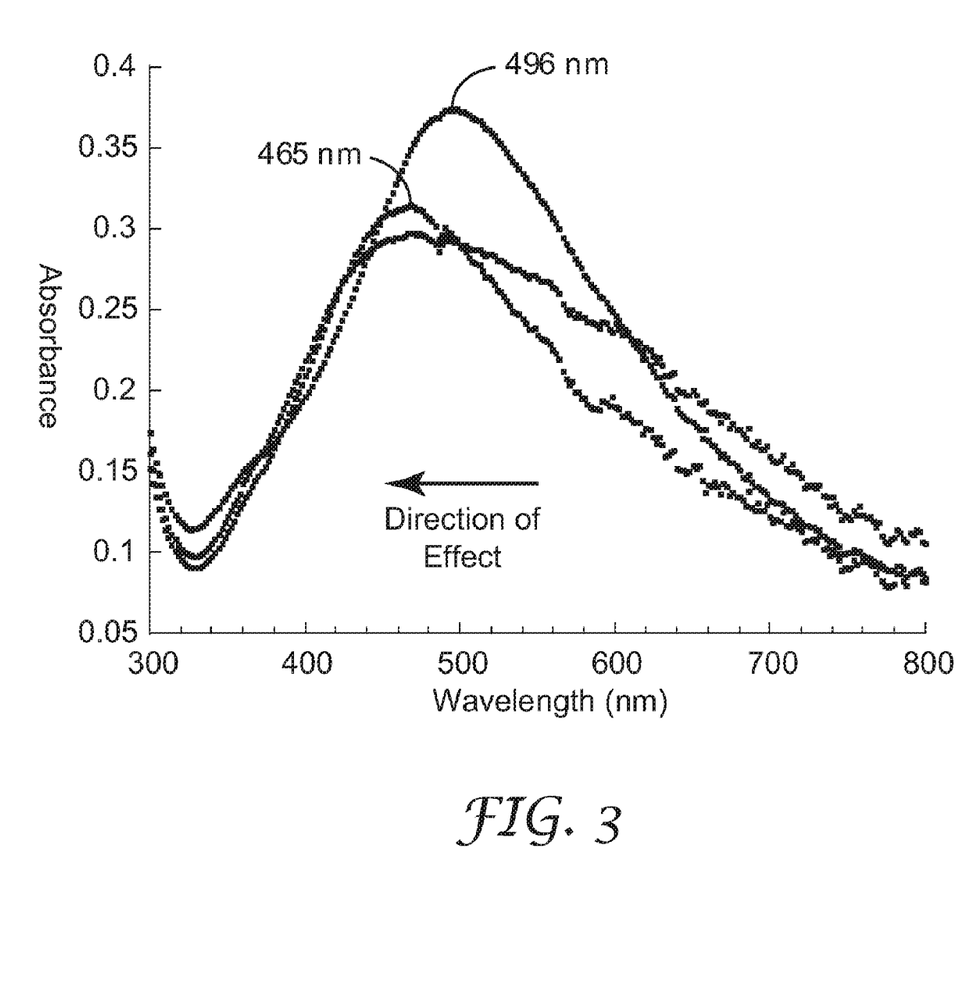
FIG. 3 is the absorbance spectra of Example 3.

Silver nanoparticles were e-beam evaporated onto BOPS film to yield a 60 Angstrom coating. The coated BOPS film had a purple tint. Samples of the coated film were stretched in an Instron tensile testing machine (Model 1122 from Instron Corp.; Canton, Mass.) with a temperature conditioning chamber set at 100° C. and a stretching rate of 0.25 centimeters per minute (0.1 inches per minute). UV Vis spectra were taken as described in Example 1 of the unstretched film, the film, stretched to 50% strain in 2 orthogonal directions, and the film stretched to 150% strain in one direction. A cross section of the coated film is shown in FIG. 1. The spectra are shown in FIG. 3, which again reveals a shift to shorter wavelengths as result of orientation, and a new absorbance peak at approximately 600 nm as result of decreased nanoparticle spacing in the direction perpendicular to orientation.

Example 4

Figure 4:
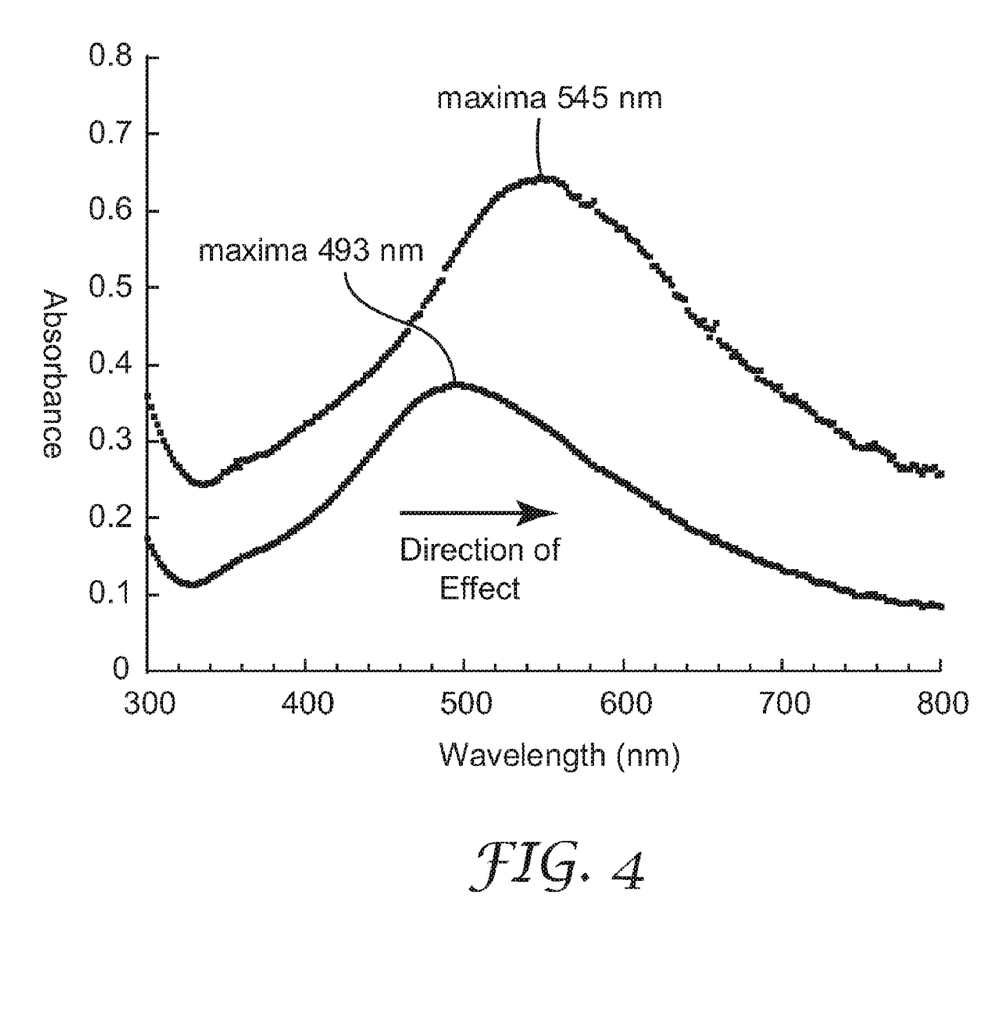
FIG. 4 is the absorbance spectra of Example 4.

Silver nanoparticles were e-beam evaporated onto BOPS Film as described in Example 3. A sample of the coated film was shrunk in an oven set at 140° C. for 5 minutes. The resulting film was had an overall shrinkage of approximately 20%. UV Vis spectra were taken as described in Example 1 of the unshrunk film and the shrunken film. The spectra are shown in FIG. 4, which reveals the absorbance peak maximum shifter to longer wavelengths as result of shrinking.

Example 5

Silver nanoparticles were e-beam evaporated onto biaxially oriented polypropylene film in the presence of oxygen to yield silver oxide (AgO surface with Ag core) nanoparticle coatings of 80 Angstroms (Sample 5A), 120 Angstroms (Sample 5B), 200 Angstroms (Sample 5C). The coated BOPP films 5A and 5B had a yellowish/amber tint while 5C had a brownish tint. The coated films were tested for surface conductivity with a Fluke 27 multimeter (John Fluke Mfc. Co. Inc, Everett, Wash.) but showed no surface conductivity. Sample 5C was placed in a 160° C. oven and shrunk by 20% and retested with multimeter and showed a resistance of 13 Kilo-Ohms when point probes were placed 1 cm apart on the surface of the specimen. This measurement was done at room temperature and approximately 30% relative humidity. The shrunken sample had a brown/gray appearance and an average of 30% transmission in the visible range.

Figure 5:
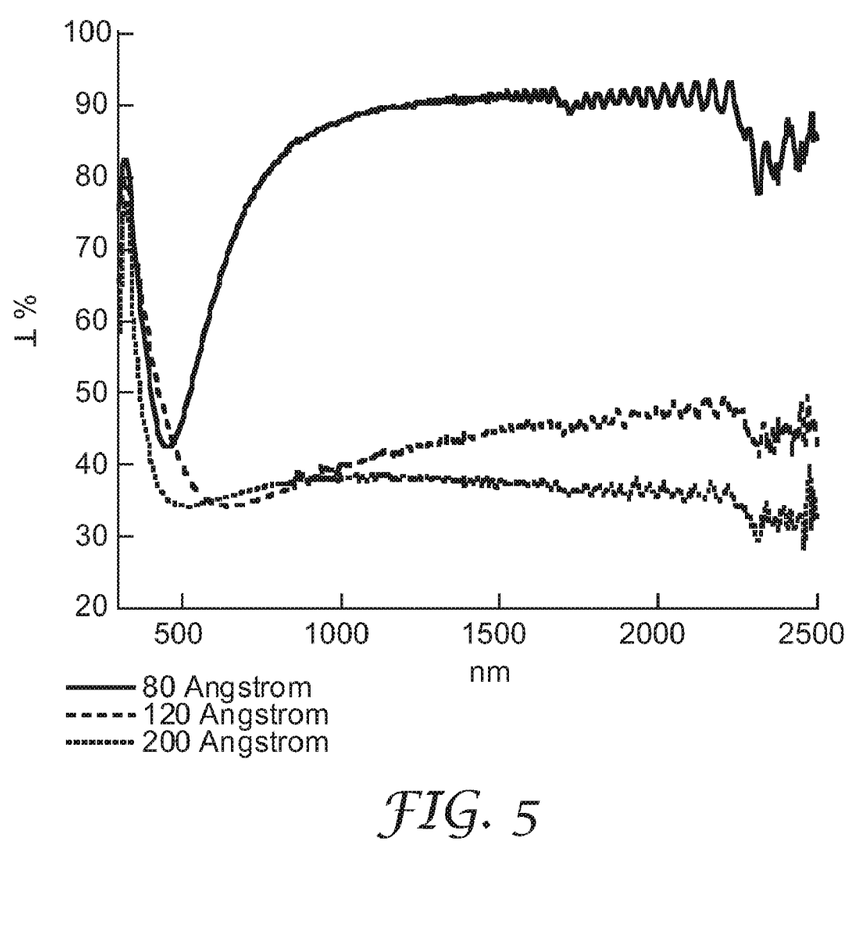
FIG. 5 is the transmission spectra of Example 5.

The transmission spectra showing the nanoparticle resonances of the initial materials is shown in FIG. 5. The plasmon absorption is observed in the 80 Angstrom sample and it is less evident in samples with low transmission as the nominal coating thickness increases. The measurements shown in this example denote the transition from a coating that is conductive and fully reflective to a non-conductive plasmonic absorptive coating. Spectra were taken using a Perkin Elmer Lamda 19 Spectrometer. Scanned at 5 nm intervals from 300-2500 nanometers (6 minutes per scan).

The invention claimed is:

1. An optical film having surface plasmon resonance comprising a thermoplastic film substrate and a discontinuous coating of metallic nanoparticles thereon wherein the absorbtion peak maximum of said optical film shifts at least 10 nm as the fiim is either further stretched or shrunk.

2. The optical film of claim 1 wherein said thermoplastic film is stretched.

3. The optical film of claim 2 wherein said stretched thermoplastic film substrate is uniaxially stretched.

4. The optical film of claim 3 wherein the total draw ratio of the stretching is at least 1.1:1.

5. The optical film of claim 2 wherein said stretched thermoplastic film substrate is biaxially stretched.

6. The optical film of claim 5 wherein the biaxially stretching is at least 1.1:1 total draw ratio.

7. The optical film of claim 5 wherein the biaxial stretching is substantially equal in longitudinal and transverse directions.

8. The optical film of claim 5 wherein the biaxial stretching is substantially nonequal in longitudinal and transverse dimensions.

9. The optical film of claim 8 wherein the absorption peak maximum are different in the longitudinal and transverse dimensions.

10. A method for preparing a metallic nanoparticle coated film comprising:
   a. providing a thermoplastic film
   b. depositing a discontinuous coating of metallic nanoparticle on the surface of the film by physical vabor deposition, and
   c. stretching or shrinking the coated film,
   wherein the absorption peak maximum of said metallic nanoparticle coated film shifts at least 10 nm as the film is either further stretched or shrunk.

11. The method of claim 10, wherein said thermoplastic film is stretched prior to said step of depositing, then further stretching or shrinking after said step of depositing.

12. The method of claim 10, wherein the metallic nanoparticles comprise individual particles or agglomerates of particles having an average major dimension of less than 100 nm.

13. The method of claim 10 wherein thee maximum average thickness of the discontinuous coating of metallic nanoparticles is less than 100 nm.

14. The method of claim 10 wherein the average mass thickness of the discontinuous coating of metallic nanoparticles is 1 to 50 nm.

15. The method of claim 10 wherein said thermoplastic film is additionally stretched prior to deposition.

16. The method of claim 10 wherein said metallic nanoparticles are selected from gold, aluminum, copper, iron, platinum, palladium, iridium, rhodium, osmium, ruthenium, titanium, cobalt, vanadium, magnesium, silver, zinc, and cadmium, indium, lanthanum, indium, lanthanum, indium tin oxide (ITO) and antimony tin oxide (ATO), antimony indium tin oxide (AITO), tin, indium, lanthanum, boron, lanthanum hexaboride, rare earth metals and mixtures and alloys thereof.

17. The method of claim 10 wherein at least 50 volume percent of the nanoparticles is exposed above the surface of the thermoplastic polymer film.

18. The method of claim 10 wherein the physical vapor deposition process is selected from vapor deposition, cathode sputtering, pyrolysis, ion plating, or e-beam deposition.

19. The method of claim 10 wherein the thermoplastic film is selected horn polyesters, polyurethanes, polyamides, polyolefins, polyamides, polystyrene, fluoropolymers, liquid crystal polymers, alkyd, melamine, urea formaldehyde, diallyl phthalate, epoxide, phenolic, polyvinyl chloride, ionomeric polymers, acrylics and silicone polymers.

20. The method of claim 10 wherein two or more metals are deposited.

21. The method of claim 10 wherein said metallic nanoparticles are metal oxide nanoparticles.

22. The method of claim 10, further comprising the step of annealing said coated film.

23. The method of claim 10 wherein the thermoplastic polymer film contains less than 1 wt. % particulate additives.

24. The method of claim 10 wherein said stretching is uniaxial.

25. The method of claim 24 wherein the stretching is at least 1.1:1.

26. The method of claim 10 wherein said stretched thermoplastic film substrate is biaxially stretched.

27. The method of claim 26 wherein the biaxially stretching is at least 1.1:1 total draw ratio.

28. The method of claim 26 wherein the biaxial stretching is substantially equal in longitudinal and transverse directions.

29. The method of claim 26 wherein the biaxial stretching is substantially nonequal in longitudinal and transverse dimensions.

30. The method of claim 10 wherein the absorption peak maximum are different in the longitudinal and transverse dimensions.

31. A sensor for use in testing biological, biochemical, chemical or environmental samples, said sensor comprising the optical film of claim 1, and a binding agent disposed over at least a portion of said metallic nanoparticle layer, wherein said binding agent interacts with a predetermined substance present in said biological, biochemical, chemical or environmental sample.

32. The sensor of claim 31 wherein said metallic nanoparticles are selected from the group consisting of gold, silver, idium, lanthanum, aluminum, copper, platinum, palladium, iridium, rhodium, osmium, ruthenium, titanium, indium, lanthanum, indium tin oxide (ITO) and antimony tin oxide (ATO), antimony indium tin oxide (AITO), tin, lanthanum, and mixtures of any two or more thereof.

33. The sensor of claim 31 wherein said reactive substance is a member of a pair selected from the group consisting of antibody/antigen; antibody/hapten; enzyme/substrate; enzyme/cofactor; enzyme/inhibitor; binding protein/substrate; carrier protein/substrate; lectin/carbohydrate; receptor/hormone; receptor/effector; nucleic acid strand/complementary nucleic acid strand; protein/nucleic acid repressor; protein/nucleic acid inducer; ligand/cell surface receptor; and virus/ligand.

34. The sensor of claim 31, wherein said functionalized material is an organosilane or an organothiol.

35. The sensor of claim 31, wherein said functionalized material is selected from the group consisting of hydrolyzed mono-, di- and trialkoxysilanes or mono-, di- an trichlorosilanes which contain at least one phosphonic acids, benzotriazoles, azlactones, —CN, —NH$_2$, 2-pyridyl, —P(C$_6$H$_5$)$_2$ and/or —SH group, and carboxyl-terminated organothiols.

36. A multilayer article comprising two or more layers of the optical film of claim 1.

37. The optical film of claim 1, wherein said nanoparticles have an aspect ratio of greater than 1.5:1.

38. The sensor of claim 31 further comprising a layer of a functionalized material disposed over at least a portion of said metallic nanoparticles; and said binding agent disposed over said layer of a functionalized material.

* * * * *

UNITED STATES PATENT AND TRADEMARK OFFICE
CERTIFICATE OF CORRECTION

PATENT NO. : 7,274,458 B2 Page 1 of 1
APPLICATION NO. : 11/073787
DATED : September 25, 2007
INVENTOR(S) : Mario A. Perez It is certified that error appears in the above-identified patent and that said Letters Patent is hereby corrected as shown below:

On the Title Page, in Col. 2, under (Other Publications)
Line 2, delete "Graphics" and insert -- Gratings --, therefor.

On the Second Page, in Col. 2, under (Other Publications)
Line 41, delete "Appplied" and insert -- Applied --, therefor.

On the Third Page, in Col. 2, under (Other Publications)
Line 24, delete "Orgamo" and insert -- Organo --, therefor.

Col. 16
Line 9, in Claim 1, delete "absorbtion" and insert -- absorption --, therefor.
Line 10, in Claim 1, delete "fiim" and insert -- film --, therefor.
Line 35, in Claim 10, delete "vabor" and insert -- vapor --, therefor.
Line 48, in Claim 13, delete "thee" and insert -- the --, therefor.

Col. 17
Line 5, in Claim 19, delete "horn" and insert -- from --, therefor.

Signed and Sealed this

Twenty-ninth Day of April, 2008

JON W. DUDAS
*Director of the United States Patent and Trademark Office*